United States Patent [19]

Liotta

[11] 3,997,562

[45] Dec. 14, 1976

[54] MACROCYCLIC POLYETHER/NITRILE COMPLEXES

[75] Inventor: Charles Leonard Liotta, Decatur, Ga.

[73] Assignee: E. I. Du Pont de Nemours and Company, Wilmington, Del.

[22] Filed: Oct. 1, 1974

[21] Appl. No.: 511,000

[52] U.S. Cl. .............................. 260/338; 260/340.3; 260/465.1; 260/465.4; 260/465.7; 260/465.8 R; 260/465.9
[51] Int. Cl.² ........................................ C07D 323/00
[58] Field of Search ............ 260/338, 340.3, 465.1, 260/465.4, 465.7, 465.8 R, 465.9

[56] References Cited

UNITED STATES PATENTS

| | | |
|---|---|---|
| 3,687,978 | 8/1972 | Pedersen ........................ 260/338 |
| 3,873,569 | 3/1975 | Pedersen ...................... 260/340.3 |

*Primary Examiner*—Norma S. Milestone

[57] ABSTRACT

Complexes of certain macrocyclic polyethers in which the polyether ring contains 18 ring atoms, 6 of which are oxygen, and the oxygen atoms are separated by 2 carbon atoms, with aliphatic nitriles having 2 to 12 carbon atoms, and the use of such complexes to obtain pure nitrile and/or pure macrocyclic polyether are disclosed.

11 Claims, No Drawings

MACROCYCLIC POLYETHER/NITRILE COMPLEXES

This invention relates to complexes of macrocyclic polyethers selected from the class consisting of 18-crown-6, monobenzo18-crown-6, dicyclohexyl-18-crown-6, and monocyclohexyl-18-crown-6, and aliphatic nitriles having 2 to 12 carbon atoms, and to the use of such complexes to obtain pure nitrile and/or the pure macrocyclic polyether.

1,4,7,10,13,16 Hexaoxacyclooctadecane, hereinafter 18-crown-6, a macrocyclic polyether, has the following formula

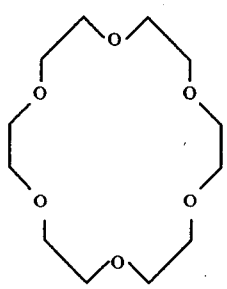

where

⌒ is a —$CH_2CH_2$— group. The compound is disclosed and claimed in U.S. Pat. No. 3,562,295, issued Feb. 9, 1971 to C. J. Pedersen. Example 1 of that patent teaches one method for the preparation of this compound. The compound is taught to be useful to complex with various metallic cations, especially alkali metal cations.

Other macrocyclic polyethers having 18 ring atoms and 6 oxygen atoms separated by 2 carbon atoms are known in the art, for example Pedersen's U.S. Pat. No. 3,687,978, J. A. C. S., Vol. 89, No. 28, pages 7017–7036 (1967). Of these various macrocyclic compounds the following will form complexes with nitriles: 18-crown-6, monocyclohexyl-18-crown-6, dicyclohexyl-18-crown-6, and monobenzo-18-crown-6.

The aliphatic nitrile which is complexed with the aforementioned macrocycle polyether should have 2 to 12 carbon atoms. The nitrile may be either a mononitrile or a dinitrile, it may be saturated or unsaturated, and may, if desired, be substituted with other radicals, such as, for example, halogens, specifically chlorine, and methoxycarbonyl. Preferred nitriles are mononitriles having 2 to 7 carbon atoms.

The complex of the macrocyclic polyether and the nitrile forms promptly when the chemicals are mixed together. The complex can be formed by mixing macrocyclic polyether in its pure form with pure nitrile, or by mixing pure macrocyclic polyether with a mixture containing the nitrile as well as impurities, or by mixing macrocyclic polyether containing impurities with pure nitrile, or by mixing macrocyclic polyether containing impurities with nitrile containing impurities. Macrocyclic polyether may be mixed with a mixture of different nitriles, thus forming a mixture of macrocyclic polyether-nitrile complexes, or nitrile may be mixed with a mixture of macrocyclic polyethers, thus forming a mixture of macrocyclic polyether nitrile complexes. The mixing can be carried out in the presence or absence of a solvent for the monocyclic polyether and the nitrile.

The complex is precipitated from the mixture in a crystalline form by conventional techniques.

The crystalline precipitate of the complex may be recovered from the remainder of the mixture by filtration or other mechanical separation. The crystalline structure of the complex differs with the particular nitrile and macrocyclic polyether, that are complexed, and sometimes with the particular technique employed to produce the crystalline precipitate. The ratio of macrocyclic polyether to nitrile in the complex may differ for different nitriles, but usually varies from 1:1 to 1:4. It is sometimes desirable to dissolve the precipitated complex in a solvent and recrystallize it, thus obtaining a purer precipitate.

The crystalline complex after separation from the remainder of the mixture may be dissociated by treating it at reduced pressure and sometimes by the application of mild heating. The use of heat will speed up the dissociation, but for some complexes, reduced pressure (partial vacuum) at room temperature is sufficient to dissociate the complex fairly rapidly. The amount of heat applied should normally be less than the amount necessary to raise the temperature above the temperature at which the macrocyclic polyether becomes unstable. It is sometimes desirable to heat the crystalline complex above its melting point to increase the speed of dissociation. The partial vacuum can vary from just below atmospheric pressure to less than about 0.1 mm of Hg.

The nitrile component of the crystalline complex is distilled off during the treatment at reduced pressure, leaving the pure macrocyclic polyether as the residue. If the crystalline complex is made up of macrocyclic polyether and only a single nitrile compound, then pure nitrile is also recovered.

When the macrocyclic polyether is soluble in water, the complex can be dissociated by contacting it with water. If in addition the nitrile is substantially insoluble in water, the nitrile will form a separate phase which can be mechanically removed.

The following Table gives the properties of various macrocyclic polyether/nitrile crystalline complexes.

TABLE

| The Nitrile | Melting Point °C in Sealed Capillary Tube | Molecular Ratio Crown:Nitrile | Physical Appearance of Precipitate | Precipitation Technique* |
| --- | --- | --- | --- | --- |
| Acetonitrile | 63.5 – 65.5 | 1:2 | Fine white crystals | Vigorous stirring of hot saturated solution in acetonitrile while cooling to room temperature |
| Acetonitrile | 72 – 75 | 1:2 | Stacked, transparent platelets | Saturated solution in acetonitrile cooled to room temperature without stirring |
| Acrylonitrile | 34.5 – 35.5 | 2:3 | Transparent cubic platelets | Saturated solution in acrylonitrile cooled and seeded with 18-crown-6/acrylonitrile complex |
| Glutaronitrile | 47 – 48 | 1:2 | Small needles | Saturated solution in glutaronitrile cooled and seeded with 18-crown-6/glutaronitrile complex |

TABLE-continued

| The Nitrile | Melting Point ° C in Sealed Capillary Tube | Molecular Ratio Crown:Nitrile | Physical Appearance of Precipitate | Precipitation Technique* |
|---|---|---|---|---|
| Adiponitrile | 50 – 52 | Uncertain | Small needles | Saturated solution in adiponitrile cooled and seeded with 18-crown-6/adiponitrile complex |
| δ-Chloro-valeronitrile | 36.5 – 38 | 1:1 | Small needles | Saturated solution in δ-chlorovaleronitrile cooled and seeded with 18-crown-6/δ-chlorovaleronitrile complex |
| 1,2-Dicyano-propane | 69 – 70.5 | 1:2 | Fine particles, color light tan | Crystallized from concentrated solution of complex in benzene |
| Succinonitrile | 83 – 84 | 1:2 | Well defined needle crystals | Precipitated by cooling solution of complex in benzene |
| Malononitrile | 127 – 129** | 1:2 | Well defined needle crystals | Precipitated by cooling solution of complex in benzene |

*The seed crystals were prepared by forming a small amount of supersaturated (at 25° C) solution in a test tube and initiating crystallization by swirling in an ice-acetone bath.
**after recrystallization from dry benzene.

EXAMPLES

EXAMPLE I

To 50 grams of crude 18-crown-6 (boiling point 125°–160° C at 0.2 mm of Hg) is a 250 ml Erlenmeyer flask is added 125 ml of acetonitrile. The resulting slurry is heated on a hot plate to effect solution. A magnetic stirring bar is added and the neck of the flask equipped with a CaSO$_4$ drying tube. The solution is stirred vigorously as it is allowed to cool to ambient temperature, and fine white crystals of crown-acetonitrile complex are deposited. The flask is finally cooled in an ice-acetone bath to precipitate as much complex as possible, and the solid then collected by rapid filtration. The hygroscopic crystals are transferred to a 500 ml round-bottom flask equipped with a magnetic stirring bar and vacuum take-off. The acetonitrile is removed from the complex at high vacuum (0.1 – 0.5 mm of Hg) with gentle heating (about 40° C) for about 3 hours. The pure, colorless crown (about 30 grams) crystallizes on standing. The crown has a melting point of 36.5°– 38.° C.

EXAMPLE II

Preparation of Acetonitrile Complex of Benzo-18-Crown-6

A solution made by dissolving 100 grams of crude benzo-18-crown-6, in 200 milliliters of acetonitrile at 40° C was treated with activated carbon and filtered under pressure. The filtrate obtained was treated again with activated carbon and filterd under pressure. The filtrate obtained this time deposited crystals on standing at room temperature, crystallization was completed at 5° C.

The acetonitrile complex of benzo-18-crown-6 was obtained as large colorless crystals. After being separated by filtration at 5° C., they were washed with cold acetonitrile and dried. Yield: 76.9 grams melting at 49°–53.8° C. Spectrum analysis indicated that the mole ratio of crown: acrylonitrile in the complex was about 1 to 2.

Recovery of Pure Benzo-18-Crown-6

A 76.5 gram portion of the crystals of the acetonitrile-benzo-18-crown-6 complex prepared above was placed in a one-liter round-bottom glass flask which was then evacuated (0.1 mm Hg) through a trap cooled with crushed solid CO$_2$. The complex decomposed, acetonitrile vapor being collected in the trap. The residual purified benzo-18-crown-6was a white powder weighing 60.2 grams and melting at 44.0°–46.5° C. Its infrared spectrum was identical with that of an authentic sample.

EXAMPLE III

Complex of 18-Crown-6 with Sebaconitrile [NC—CH$_2$)$_8$—CN]

18-Crown-6 (5.28 g, 0.02 mol) was added to sebaconitrile (3.28 g, 0.02 mol). The sebaconitrile was more than three years old and yellow in color. The mixture was swirled in a steam-heated water bath for 4 minutes until no more solid remained. Crystals formed spontaneously when the yellow liquid was cooled to room temperature. The solid was dissolved in the minimum volume of butyl chloride in a 40° C water bath, and the solution was filtered. The filtrate was allowed to cool to room temperature and was then cooled successively in an ice-wate bath and in an ice-acetone bath. The precipitated white solid was filtered, washed once with butyl chloride which had been cooled in a crushed solid carbon dioxide-acetone bath, and dried with suction under a stream of nitrogen to give 5.62 g of the complex, melting point 50.5°–53.5° C. The proton nuclear magnetic resonance spectrum of the complex, determined in deuteriochloroform, indicated that 18-crown-6 and sebaconitrile are present in the complex in a molecular ratio of approximately 1:1.

Isolation of Sebaconitrile from its Complex with 18-Crown-6

Water (5.0 ml) was added to 2.18 g of the sebaconitrile-18-crown-6 complex. The mixture was stirred for a few seconds until solid was no longer present. After the mixture had been allowed to stand for several minutes, it was observed to comprise an upper and a lower layer. Most of the oily upper layer was removed with a pipet; it weighed 0.78 g (some of the upper layer was lost in transfer). The oily liquid was washed with four 3-ml portions of water and was dried for several hours over anhydrous sodium sulfate. The infrared spectrum of the colorless liquid matched the spectrum of the yellow sample of sebaconitrile which had been used to prepare the complex employed in this experiment.

EXAMPLE IV

Preparation of a Complex of Dicyclohexyl-18-Crown-6 with Acetonitrile

About 1 ml of acetonitrile was added to 2.34 g of dicyclohexyl-18-crown-6 (a mixture of syn- and anti-isomers) having a purity by gas chromatography of 99.41%. The mixture was heated on a steam bath and more acetonitrile was added until all the solid had dissolved. The total weight of acetonitrile added was 2.21 g. The solution was cooled in an ice bath and was vigorously stirred. After about half a minute, a white precipitate formed. The solid was filtered, washed twice with acetonitrile which had been cooled to its freezing point by a mixture of crushed solid carbon dioxide and acetone, and was dried by suction under a stream of nitrogen. The slightly gummy solid weighed 1.79 g and melted at 34°–55° C. Spectrum analysis indicated that dicyclohexyl-18-crown-6 and acetonitrile were present in a molecular ratio of approximately 1:3.

A portion of the complex was recrystallized from acetonitrile; the purified solid was collected on a porous clay plate and was rapidly air dried. It melted at 48.0°–58.0° C.

EXAMPLE V

Purification of 18-Crown-6-via an Acetonitrile Complex by Vacuum Separation at Room Temperature Acetonitrile (78 ml) was manually stirred in an ice bath while 78.3 g of crude 18-crown-6, boiling point 138°–155° C/0.35 mm, was added. The white precipitate of the 1:2, 18-crown-6:acetonitrile complex was filtered, successively washed with 35 ml and 50 ml portions of acetonitrile which had been cooled to its freezing point, and dried under a stream of nitrogen. Yield: 58.3 g; melting point 70.0°–73.5° C.

The complex (57.8 g) was placed into a vacuum desiccator at room temperature, and the acetonitrile was removed by pumping on the desiccator with an oil pump for 16 hours at a pressure of 0.1 mm. There remained in the desiccator 44.4 grams of 18-crown-6, a white solid melting at 37.2°–37.7° C, 99.9% pure by gas chromatography. Calculated for $C_{12}H_{24}O_6$: C 54.5%, H 9.2%. Found: C 54.8%, H 9.4%. The weight loss during pumping represents 97.8% of the theoretical weight of acetonitrile contained in the 1:2 18-crown-6:acetonitrile complex.

In a separate experiment, the crude 18-crown-6 (from triethylene glycol and 1,8-dichloro-3,6-dioxaoctane), boiling point 130.0° C/0.4 – 160.0° C/0.5 mm, showed a band at 3300 cm$^{-1}$ in its infrared spectrum, indicating contamination with a hydroxylic impurity. Purification by the same procedure described above gave pure 18-crown-6, melting point 36.6°–38.1° C, with no absorption at 3300 cm$^{-1}$ in its infrared spectrum.

EXAMPLE VI

A complex of 18-crown-6 and methyl cyano acetate was prepared by the technique demonstrated in example V. The complex was recrystallized from butyl chloride and had a melting point of 53.5° to 59.5° C. The ratio of crown to nitrile in this complex was about 1 to 2 to 1 to 3.

EXAMPLE VII

A complex of monocyclohexyl-18-crown-6 and acetonitrile was prepared at room temperature. The complex was precipitated with dry ice. The complex had a melting point of 22°–31° C and the ratio of crown to acrylonitrile was about 1 to 4.

I claim:
1. A complex of a macrocyclic polyether selected from the class consisting of 18-crown-6, monobenzo-18-crown-6, dicyclohexyl-18-crown-6, and monocyclohexyl-18-crown-6 and an aliphatic nitrile having 2 to 12 carbon atoms and selected from the class consisting of saturated and unsaturated mononitriles and dinitriles which are unsubstituted or substituted with radicals selected from the class consisting of halogens and methoxycarbonyl.
2. A complex of claim 1 in which the aliphatic nitrile is unsaturated.
3. A complex of claim 1 in which the nitrile is halogen substituted.
4. A complex of claim 1 in which the nitrile is a mononitrile and contains 2 to 7 carbon atoms.
5. A complex of claim 1 in which the nitrile is acrylonitrile.
6. A process for obtaining a purified macrocyclic polyether selected from the class consisting of 18-crown-6, monobenzo-18-crown-6, dicyclohexy-18-crown-6, and monocyclohexyl-18-crown-6 and/or a purified aliphatic nitrile having 2 to 12 carbon atoms and selected from the class consisting of saturated and unsaturated mononitriles and dinitriles which are unsubstituted or substituted with radicals selected from the class consisting of halogens and methoxycarbonyl, which comprises mechanically separating a complex of the macrocyclic polyether and the nitrile from a mixture containing the complex, dissociating the complex and separating the components from each other.
7. The process of claim 6 in which the complex is dissociated by the application of partial vacuum, and the components separated by distillation.
8. The process of claim 6 in which the complex is separated from the mixture containing the complex by filtration.
9. The complex of claim 1 in which the nitrile is acetonitrile.
10. The complex of claim 1 in which the nitrile is adiponitrile.
11. The process of claim 6 in which the complex is water soluble and it is dissociated by contacting the complex with water, and the nitrile component of the complex is then removed mechanically.

* * * * *